(12) United States Patent
Soboleski et al.

(10) Patent No.: US 8,070,777 B2
(45) Date of Patent: Dec. 6, 2011

(54) METHOD AND DEVICE FOR TREATING ABNORMAL CURVATURE OF A SPINE

(75) Inventors: Donald A. Soboleski, Sydenham (CA); Gerald A. B. Saunders, Sydenham (CA); Daniel P. Borschneck, Glenburnie (CA)

(73) Assignee: Queen's University at Kingston, Kingston, Ontario (CA)

( * ) Notice: Subject to any disclaimer, the term of this patent is extended or adjusted under 35 U.S.C. 154(b) by 470 days.

(21) Appl. No.: 12/068,850

(22) Filed: Feb. 12, 2008

(65) Prior Publication Data

US 2008/0287996 A1 Nov. 20, 2008

Related U.S. Application Data

(63) Continuation of application No. 10/075,373, filed on Feb. 15, 2002, now Pat. No. 7,371,238.

(60) Provisional application No. 60/268,860, filed on Feb. 16, 2001.

(51) Int. Cl.
*A61B 17/70* (2006.01)
(52) U.S. Cl. ...................................................... 606/247
(58) Field of Classification Search .... 623/17.11–17.16; 606/246–249
See application file for complete search history.

(56) References Cited

U.S. PATENT DOCUMENTS

| | | | |
|---|---|---|---|
| 3,745,590 A * | 7/1973 | Stubstad | 623/13.11 |
| 3,824,995 A * | 7/1974 | Getscher et al. | 606/281 |
| 3,867,728 A | 2/1975 | Stubstad et al. | |
| 3,875,595 A | 4/1975 | Froning | |
| 3,879,767 A | 4/1975 | Stubstad | |
| 4,001,896 A | 1/1977 | Arkangel | |
| 4,085,466 A | 4/1978 | Goodfellow et al. | |
| 4,156,296 A | 5/1979 | Johnson et al. | |
| 4,231,121 A | 11/1980 | Lewis | |
| 4,349,921 A | 9/1982 | Kuntz | |
| 4,502,161 A | 3/1985 | Wall | |
| 4,714,469 A | 12/1987 | Kenna | |
| 4,759,769 A | 7/1988 | Hedman et al. | |
| 4,772,287 A | 9/1988 | Ray et al. | |
| 4,863,477 A | 9/1989 | Monson | |
| 4,904,260 A | 2/1990 | Ray et al. | |
| 4,911,718 A | 3/1990 | Lee et al. | |

(Continued)

FOREIGN PATENT DOCUMENTS

DE 9304368 U 6/1993

(Continued)

OTHER PUBLICATIONS

Kirkaldy-Willis, W.H., et al., "Pathology and pathogenesis of lumbar spondylosis and stenosis", Spine 3(4): 319-328 (Dec. 1978).

(Continued)

*Primary Examiner* — Anu Ramana
(74) *Attorney, Agent, or Firm* — Stephen J. Scribner; Carol Miernicki Steeg

(57) ABSTRACT

This invention relates to a spinal facet cap for treating scoliosis, the facet cap comprising a shim portion for inserting into a facet joint of a spine, and an alignment portion for maintaining alignment of the shim portion within the facet joint. The invention also provides a method for treating scoliosis, comprising implanting at least one spinal facet cap into at least one facet joint of a subject in need thereof.

10 Claims, 10 Drawing Sheets

U.S. PATENT DOCUMENTS

| | | |
|---|---|---|
| 5,015,255 A | 5/1991 | Kuslich |
| 5,047,055 A | 9/1991 | Bao et al. |
| 5,062,845 A | 11/1991 | Kuslich |
| 5,071,437 A | 12/1991 | Steffee |
| 5,092,866 A | 3/1992 | Breard et al. |
| 5,127,912 A | 7/1992 | Ray et al. |
| 5,147,404 A | 9/1992 | Downey |
| 5,171,280 A | 12/1992 | Baumgartner |
| 5,192,326 A | 3/1993 | Bao et al. |
| 5,258,031 A | 11/1993 | Salib et al. |
| 5,300,073 A | 4/1994 | Ray et al. |
| 5,306,275 A | 4/1994 | Bryan |
| 5,306,308 A | 4/1994 | Gross et al. |
| 5,306,309 A | 4/1994 | Wagner et al. |
| 5,360,431 A | 11/1994 | Puno et al. |
| 5,370,697 A | 12/1994 | Baumgartner |
| 5,401,269 A | 3/1995 | Buttner-Janz et al. |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,491,882 A | 2/1996 | Walston et al. |
| 5,507,823 A | 4/1996 | Walston et al. |
| 5,514,180 A | 5/1996 | Heggeness et al. |
| 5,527,312 A | 6/1996 | Ray |
| 5,527,314 A | 6/1996 | Brumfield et al. |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,571,189 A | 11/1996 | Kuslich |
| 5,571,191 A | 11/1996 | Fitz |
| 5,577,995 A | 11/1996 | Walker et al. |
| 5,591,165 A | 1/1997 | Jackson |
| 5,603,713 A | 2/1997 | Aust et al. |
| 5,645,597 A | 7/1997 | Krapiva |
| 5,645,599 A | 7/1997 | Samani |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,683,464 A | 11/1997 | Wagner et al. |
| 5,702,450 A | 12/1997 | Bisserie |
| 5,716,415 A | 2/1998 | Steffee |
| 5,741,261 A | 4/1998 | Moskovitz et al. |
| 5,766,251 A | 6/1998 | Koshino |
| 5,766,253 A | 6/1998 | Brosnahan, III |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,876,404 A | 3/1999 | Zucherman et al. |
| 5,879,396 A | 3/1999 | Walston et al. |
| 5,893,889 A | 4/1999 | Harrington |
| RE36,221 E | 6/1999 | Breard et al. |
| 5,951,555 A | 9/1999 | Rehak et al. |
| 6,001,130 A | 12/1999 | Bryan et al. |
| 6,014,588 A | 1/2000 | Fitz |
| 6,019,792 A | 2/2000 | Cauthen |
| 6,039,763 A | 3/2000 | Shelokov |
| 6,048,342 A | 4/2000 | Zucherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,099,531 A | 8/2000 | Bonutti |
| 6,113,637 A | 9/2000 | Gill et al. |
| 6,132,464 A | 10/2000 | Martin |
| 6,132,465 A | 10/2000 | Ray et al. |
| 6,200,322 B1 | 3/2001 | Branch et al. |
| 6,293,949 B1 | 9/2001 | Justis et al. |
| 6,419,703 B1 | 7/2002 | Fallin et al. |
| 6,436,101 B1 | 8/2002 | Hamada |
| 6,470,207 B1 | 10/2002 | Simon et al. |
| 6,565,605 B2 | 5/2003 | Goble et al. |
| 6,579,318 B2 | 6/2003 | Varga et al. |
| 6,579,319 B2 | 6/2003 | Goble et al. |
| 6,610,091 B1 | 8/2003 | Reiley |
| 6,669,729 B2 | 12/2003 | Chin |
| 6,761,720 B1 | 7/2004 | Senegas |
| 6,764,491 B2 | 7/2004 | Frey et al. |
| 6,783,527 B2 | 8/2004 | Drewry et al. |
| 6,811,567 B2 | 11/2004 | Reiley |
| 6,902,566 B2 | 6/2005 | Zucherman et al. |
| 6,974,478 B2 | 12/2005 | Reiley et al. |
| 7,101,375 B2 | 9/2006 | Zucherman et al. |
| 7,371,238 B2 | 5/2008 | Soboleski et al. |
| 2001/0018614 A1 | 8/2001 | Bianchi |
| 2002/0029039 A1 | 3/2002 | Zucherman et al. |
| 2002/0151895 A1 | 10/2002 | Soboleski et al. |
| 2003/0004572 A1 | 1/2003 | Goble et al. |
| 2003/0187454 A1 | 10/2003 | Gill et al. |
| 2004/0059429 A1 | 3/2004 | Amin et al. |
| 2004/0116927 A1 | 6/2004 | Graf |
| 2004/0127989 A1 | 7/2004 | Dooris et al. |
| 2004/0143264 A1 | 7/2004 | McAfee |
| 2004/0230201 A1 | 11/2004 | Yuan et al. |
| 2004/0230304 A1 | 11/2004 | Yuan et al. |
| 2005/0010291 A1 | 1/2005 | Stinson et al. |
| 2005/0049705 A1 | 3/2005 | Hale et al. |
| 2005/0159746 A1 | 7/2005 | Grob et al. |
| 2006/0111780 A1 | 5/2006 | Petersen et al. |
| 2006/0200137 A1 | 9/2006 | Soboleski et al. |
| 2007/0055373 A1 | 3/2007 | Hudgins et al. |
| 2007/0135814 A1 | 6/2007 | Farris |
| 2007/0179619 A1 | 8/2007 | Grob et al. |

FOREIGN PATENT DOCUMENTS

| | | |
|---|---|---|
| DE | 20112123 | 10/2001 |
| DE | 10135771 A1 | 2/2003 |
| FR | 2722980 | 2/1996 |
| JP | 10179622 A2 | 7/1998 |
| WO | WO 98/48717 | 11/1998 |
| WO | WO 99/23963 A1 | 5/1999 |
| WO | WO 00/38582 A1 | 7/2000 |
| WO | WO 00/53126 | 9/2000 |
| WO | WO 01/30248 A1 | 5/2001 |
| WO | WO 03/101350 A1 | 12/2003 |
| WO | WO 2004/071358 A1 | 8/2004 |
| WO | WO 2006/058018 | 6/2006 |

OTHER PUBLICATIONS

Kotani, Y., et al., "The effects of spinal fixation and destabilization on the biomechanical . . . ligaments: An in vivo study", Spine 23(6): 672-682 (Mar. 15, 1998).

Lemaire, J.P., et al., "Intervertebral disc prosthesis: results and prospects for the year 2000", Clinical Orthopaedics and Related Research, 337: 64-76 (1997).

Lombardi, J.S., et al., "Treatment of degenerative spondylolisthesis", Spine 10(9): 821-827 (1985).

McMillin, C.R., et al., "Artificial spinal discs with up to five years follow-up", 20th Annual Meeting of the Society for Biomaterials (Abstract) p. 89 (Apr. 5-9, 1994).

Nagata, H., et al., "The effects of immobilization of long segments of the spine on the adjacent and distal . . . motion", Spine 18(16): 2471-2479 (1993).

Posner, I., et al., "A biomechanical analysis of the clinical stability of the lumbar and lumbosacral spine", Spine 7(4): 374-389 (1982).

Rosenberg, N.J., "Degenerative spondylolisthesis—predisposing factors", The Journal of Bone and Joint Surgery 57-A(4): 467-474 (1975).

Szpalski, M., et al., "Spine arthroplasty: a historical review", Eur Spine J. 11 (2): S65-S84 (Aug. 13, 2002).

Tsantrizos, A., et al., "Segmental stability and compressive strength of posterior lumbar interbody fusion implants", Spine 25(15): 1899-1907 (2000).

Dickson, R.A., "The etiology and pathogenesis of idiopathic scoliosis", Acta Orthopaedica Belgica 58(1): 21-25 (1992).

Dickson, R.A., "The scientific basis of treatment of idiopathic thoracic scoliosis", Acta Orthopaedica Belgica 58(Suppl. 1): 107-110 (1992).

Millner, P.A., et al., "Idiopathic scoliosis: biomechanics and biology", Eur. Spine J. 5: 362-373 (1996).

Mohaideen, A., et al., "Not all rods are Harrington—an overview of spinal instrumentation in scoliosis treatment", Pediatr. Radiol. 30: 110-118 (2000).

Smith, R.M., et al., "Experimental structural scoliosis", The Journal of Bone and Joint Surgery, 69: 576-581 (1987).

Chiu, J.C., et al., "Translaminar facet fixation: an alternative method for lumbar fusion: . . . cases", http://www.spinecenter.com/papers/facet/facet.htm, 12 pages (Sep. 8, 2005).

Van Schaik, Jan P.J., et al., "Curvature of the lower lumbar facet joints: variations at different . . . orientation", Journal of Spinal Disorders, 12(4): 341-347 (1999).

Lu, J., et al., "Translaminar facet screw placement: an anatomic study", The American Journal of Orthopedics, 550-555 (Aug. 1998).

Ebraheim, N.A., et al., "The quantitative anatomy of the thoracic facet and the posterior projection of its inferior facet", Spine 22(16): 1811-1818 (1997).

Panjabi, M.M., et al., "Articular facets of the human spine, quantitative three-dimensional anatomy", Spine 18(10): 1298-1310 (1993).

Boden, S.D., et al., "Orientation of the lumbar facet joints: association with degenerative disc disease", The Journal of Bone and Joint Surgery 78-A(3): 403-411 (Mar. 1996).

Cavanaugh, J.M., et al., "Lumbar facet pain: biomechanics neuroanatomy and neurophysiology", Survey Article, J. Biomechanics 29(9): 1117-1129 (1996).

Yoganandan, N., et al., "Anatomic study of the morphology of human cervical facet joint", Spine 28(20): 2317-2323 (2003).

Dudley, et al., "Spinal injuries", Rod & Smith's Operataive Surgery—Orthopaedics Part 1, London: Butterworth-Heinemann: 637-641 (1991).

Argenson, C., et al., "A scheme for the . . . injuries", available at http://www.maitrise-orthop.com/corpusmaitri/orthopaedic/mo61_spine_injury_class/spine_injury.shtml, 26 pages, Feb 1997.

Levine, A.M., et al., "Management of fracture separations of the articular mass using porterior cervical plating", Spine 17: S447-S454 (1992).

Shapiro, S., et al., "Outcome of 51 cases of unilateral locked cervical facets: interspinous . . . with iliac crest", Journal of Neurosurgery 19: 19-24 (1999).

* cited by examiner

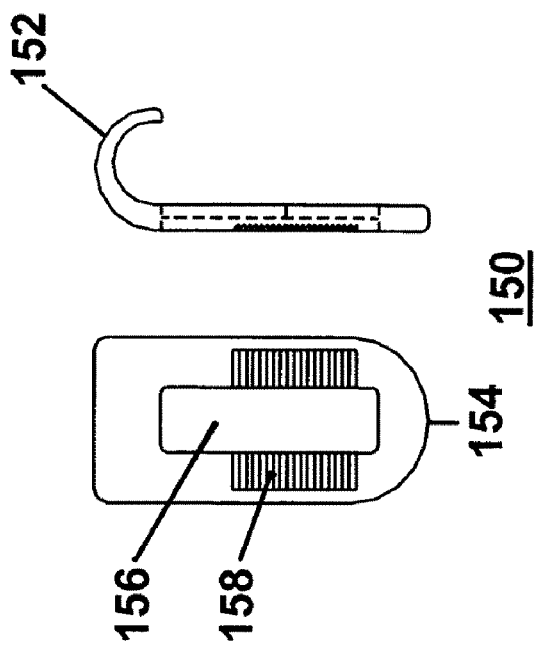
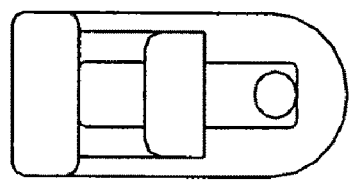
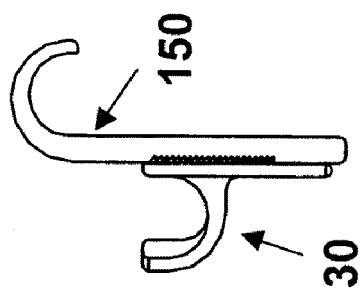
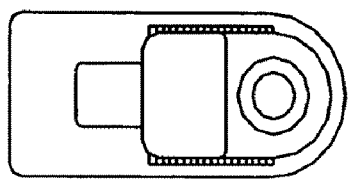
FIGURE 5A
FIGURE 5B
FIGURE 5C

METHOD AND DEVICE FOR TREATING ABNORMAL CURVATURE OF A SPINE

RELATED APPLICATION

This application is a continuation of U.S. patent application Ser. No. 10/075,373, filed on Feb. 15, 2002, now U.S. Pat. No. 7,371,238, issued May 13, 2008, and claims the benefit of the filing date of U.S. Provisional Application No. 60/268,860, filed on Feb. 16, 2001, the contents of which are incorporated herein by reference in their entirety.

BACKGROUND OF THE INVENTION

Scoliosis is an orthopedic condition characterized by abnormal curvature of the spine, with varying degrees of lateral curvature, lordosis and rotation. Despite extensive research, the pathogenesis of scoliosis remains obscure in the majority of cases.

The vertebral column is composed of vertebra, discs, ligaments and muscles. Its function is to provide both mobility and stability of the torso. Mobility includes rotation, lateral bending, extension and flexion. Scoliotic curvature is associated with pathologic changes in the vertebra and related structures. Vertebral bodies become wedge-shaped, pedicles and laminas become shorter and thinner on the concave aspect of the curve. Apart from the obvious physical deformity, cardiopulmonary problems may also present. As curvature increases, rotation also progresses causing narrowing of the chest cavity. In severe deformities, premature death is usually caused by respiratory disease and superimposed pneumonia.

Treatment options have varied little over the past few decades, and only two treatments effectively help correct scoliosis: spinal bracing with exercises and surgery. A properly constructed Milwaukee or low-profile brace will aid some patients with minor scoliosis. However, if the scoliosis progresses despite such bracing, or if there is substantial discomfort, surgical correction involving fusion of vertebra may be required. Surgery has traditionally involved procedures such as the Harrington, Dwyer and Zielke, and Luque procedures which rely on implanted rods, laminar/pedicle hooks, and screws to maintain the correction until stabilized by fusion of vertebrae.

Thus the goal of current surgery is to strip the paraspinal muscles from the lamina of vertebra to be fused, and effect correction and spinal fusion in one step. The general technique is as follows:

1. The outer cortex of the lamina and spinous processes is removed so that raw cancellous bone is exposed.
2. Posterior facet joints are destroyed and usually autogenous bone graft added. Graft is usually placed along the entire fusion area. The fusion extends from one vertebra above the superior end-vertebra involved in the curvature to two below the inferior end-vertebra of the curve.
3. Spinal instrumentation is applied. A distraction rod allows the spine to be 'jacked' up on the concave side of the curve. A compression assembly may be used on the convex side of the curve to 'pull' the curve straight. Anchors, laminar hooks, and/or wires are placed around the lamina to provide fixation for the rods.

Yet other surgical procedures involve memory metal implants (Sanders, *A Memory Metal Based Scoliosis Correction System*, CIP-Data Koninklijke Bibliotheek, Den Haag, 1993), fusion of vertebra anteriorly, using anterior cages (e.g., Harms cage, from DePuy-AcroMed Inc.). Nevertheless, it is clear that available procedures have drawbacks including the requirement for substantial prosthetic implants (see Mohaideen et al., Pediatr. Radiol. 30:110-118 (2000) for a review) and complicated surgical procedures, often only partly correct scoliotic deformities, and result in reduced flexibility of the spine.

SUMMARY OF THE INVENTION

According to one aspect of the present invention there is provided a spinal facet cap for treating scoliosis, comprising a shim portion for inserting into a facet joint of a spine, and an alignment portion for maintaining alignment of said shim portion within said facet joint. The shim portion of the spinal facet cap comprises two opposed surfaces for engaging articular surfaces of the facet joint. In one embodiment, the shim portion is of substantially uniform thickness. In another embodiment, the shim portion is wedge-shaped.

In one embodiment of the spinal facet cap, the alignment portion comprises a tongue. In some embodiments, the tongue is provided with an orifice.

In another embodiment, the alignment portion comprises a boss along at least one edge of the shim portion.

In yet another embodiment, the alignment portion comprises at least one facet hook disposed along at least one edge of the shim portion, for receiving either one of the superior facet or the inferior facet of a vertebra. In a further embodiment, the alignment portion comprises two facet hooks disposed along two edges of the shim portion, one said facet hook for receiving the superior facet of a first vertebra, a second said facet hook for receiving the inferior facet of a second vertebra. In further embodiments in which facet hooks are provided, the alignment portion further comprises a tongue having an orifice. In yet further embodiments, the thickness of the wedge-shaped shim portion, and/or the distance between alignment portions disposed on either side of the shim portion, is adjustable.

According to another aspect of the present invention there is provided a method for treating scoliosis in a subject in need thereof comprising implanting in a facet joint of the subject a spinal facet cap, said spinal facet cap comprising a shim portion and an alignment portion for maintaining alignment of said facet cap within said facet joint, such that scoliosis in the subject is treated. In some embodiments, a spinal facet cap is implanted in each of two or more facet joints of the subject, such that scoliosis in the subject is treated.

In some embodiments of the method of the invention, the alignment portion comprises at least one facet hook disposed along at least one edge of the shim portion, for receiving either one of the superior facet or the inferior facet of a vertebra.

In other embodiments, the method further comprises evaluating the subject for the number, size, shape, location, and placement of spinal facet caps required to treat scoliosis in the subject. In yet other embodiments, an imaging system is used to so evaluate the subject. In some embodiments, the imaging system is a computed tomography (CT) system.

BRIEF DESCRIPTION OF THE DRAWINGS

The invention will be described, by way of example, with reference to the accompanying drawings, wherein:

FIG. 5 shows a further embodiment of a spinal facet cap according to the invention;

DETAILED DESCRIPTION OF THE INVENTION

Figure 1:
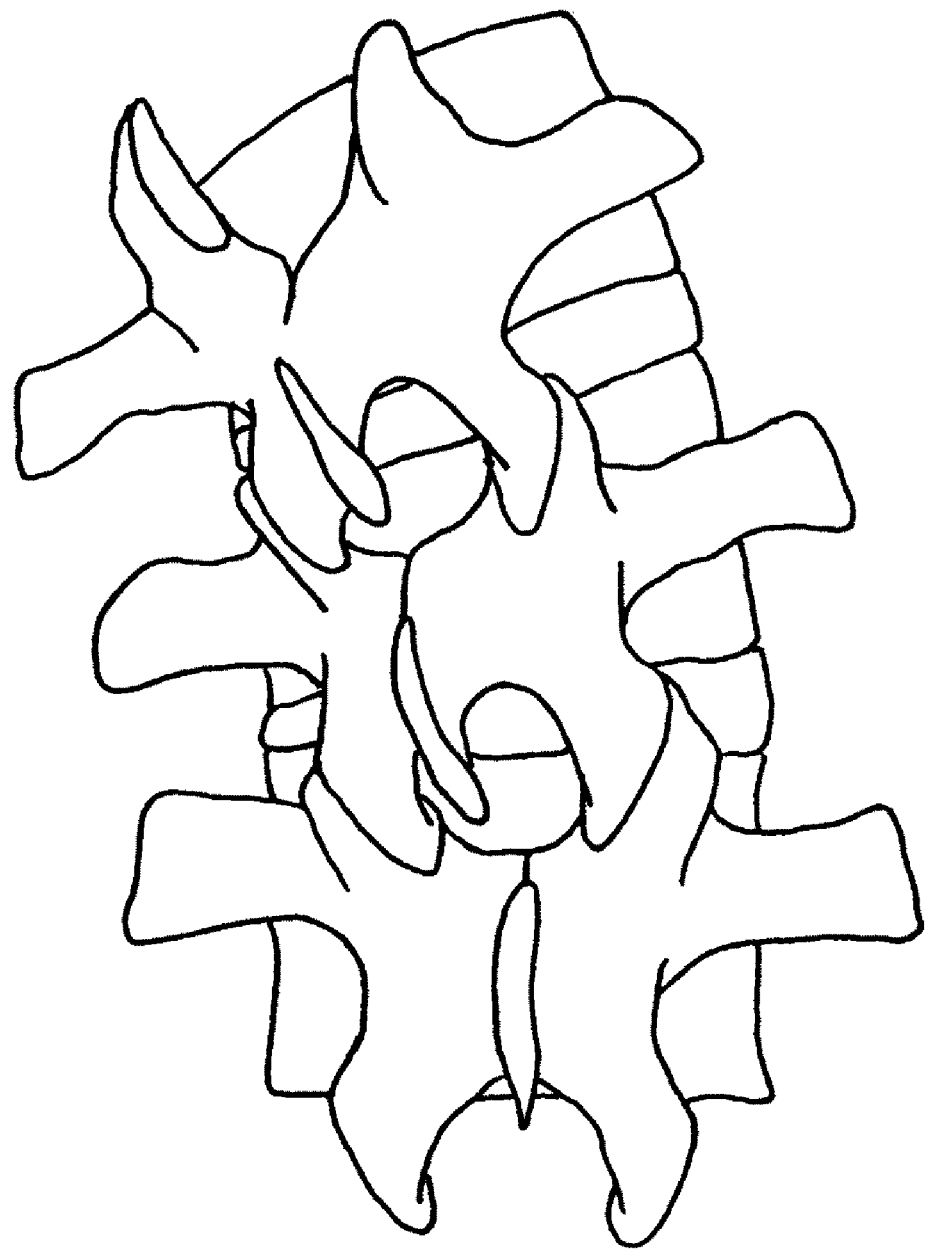
FIG. 1 shows a posterior view of a typical scoliotic spine.

Surgical procedures for correction of scoliosis has changed little in the last forty years. Current procedures still rely on surgical principals established in the 1960's, and involve fusion of one or more vertebrae.

Selection for the level of fusion requires analysis about a plum line from the sacral spinous process superior. Vertebrae that pass outside this line identify the curve. The most superior of the inferior vertebrae, which bisect this line, is the inferior extent for fusion and the most inferior of the superior vertebrae that bisect this line is the superior extent of fusion. All levels in-between these two identified levels require fusion.

After the curve is identified, all posterior ligaments and facet joints are destroyed by decortication and cartilage is removed at each level of fusion. Instrumentation for correction of the scoliosis is placed in such a manner to apply a distractive force on the concavity of the curve and compression on the convexity of the curve. All current systems rely on some vertebral fixation to a rod. Compressive and distractive forces are then applied along the rod at the points of vertebrae to rod fixation.

Three forms of fixation of the posterior spine are currently available: pedicle/laminar hooks, wires and screws. Laminar hooks are placed around vertebrae lamina. Distractive hooks are placed pointing away from the apex of the curve and compressive hooks placed facing towards the apex of the curve. Pedicle screws are placed posterior to anterior in the vertebrae and can either have a distractive or compressive force applied through the rod. Laminar wires wrap around the lamina and connect to a rod at each level. The corrective force is applied as the wire tightens around a rigid rod. The lamina and thus the vertebrae are dragged to the rod.

The spinal facet cap of the invention differs from the above-described standard instrumentation in a number of ways. For example, as discussed above, during standard procedures for correcting scoliosis, facet joints are generally destroyed. In contrast, the spinal facet caps of the invention require that the facet joints are substantially or entirely intact. This procedure is thus expected to preserve mobility of the facet joint. Further, rather than applying a distractive or compressive force through a rod, the facet cap effectively reshapes the facet joint. Such reshaping affords symmetry between left and right facet joints which corrects abnormal curvature. Thus, no fixation of the vertebrae is required; rather, there is modulation of the vertebral (facet) shape. This reshaping is expected to allow for the omission of fusing the intervening vertebral levels and multiple levels of vertebrae, which is the result of rod fixation, thus preserving flexibility of the spine. Also, the use of conventional instrumentation with a rod concentrates the load (i.e., weight of the torso) on the portion of the spine to which the rod is attached, as well as on the rod itself. The resulting stress sometimes results in failure of the conventional instrumentation. In contrast, in providing for the correction of individual facet joints of the spine, the facet cap of the invention maintains the natural load distribution along the spine. Accordingly, there is no load concentration at any point of the spine, and low likelihood of failure of the implanted facet cap.

As used herein, the term "scoliosis" is intended to mean any abnormal curvature of the spine. Such abnormal curvature can exist in any one of all three planes, or in any combination thereof, and hence can be manifested by inappropriate lateral curvature, lordosis, kyphosis, and/or rotation. Scoliosis can be congenital or idiopathic, or induced by injury, trauma, infection, inflammation, or degenerative changes in the spine.

As used herein, the term "treating scoliosis" is intended to mean correcting or reducing curvature of the spine of a subject, such that the subject experiences an improvement in condition, comfort (e.g., reduction or amelioration of pain), appearance, posture, and/or flexibility of the spine. The term "treating scoliosis" is also intended to mean preventing scoliosis from progressing to a more severe state, or inhibiting the degree to which scoliosis progresses.

As used herein, the term "subject" is intended to mean any vertebrate that can have scoliosis. Typically, such subjects are primates. Preferably, the subject is human.

According to one theory, many forms of scoliosis result from asymmetry between left and right facet joints of vertebrae. According to another theory, many forms of scoliosis cause asymmetry between left and right facet joints of vertebrae. While not holding to one particular theory at the exclusion of others, the present invention provides for the treatment of scoliosis by substantially or completely correcting such asymmetry.

In one aspect, the invention provides a prosthetic device for treating scoliosis by substantially or completely correcting asymmetry between left and right facet joints of vertebrae. The prosthetic device, generally referred to as a spinal facet cap, is surgically implanted into a spinal facet joint at any level in the spine. Surgically implanting one or more spinal facet cap(s) is carried out with minimal or no modification of the facet joint(s) involved; thus, the invention provides for the correction of left-right asymmetry of facet joints while preserving the facet joints. In this respect the invention is unlike any known procedures for treating scoliosis.

Figure 2:
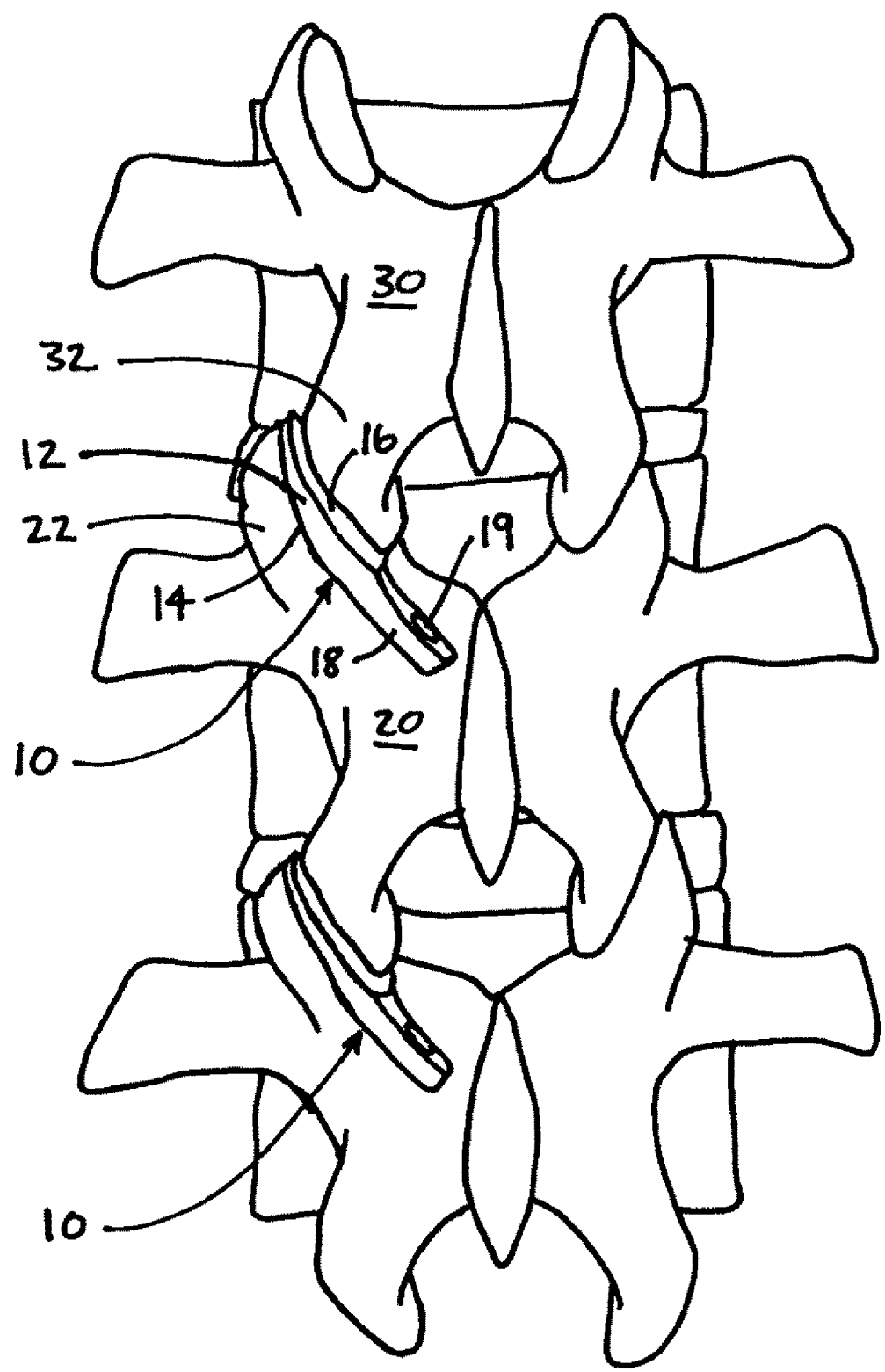
FIG. 2 shows a posterior view of a scoliotic spine corrected with spinal facet caps according to the invention.

FIG. 1 shows a posterior view of a typical scoliotic spine, with asymmetry between left and right facet joints, and spinal curvature convex left. FIG. 2 shows the spine of FIG. 1 in which the asymmetry between left and right facet joints has been corrected with two spinal facet caps according to an embodiment of the present invention. As can be seen in FIG. 2, a spinal facet cap 10 according to the invention comprises a shim portion 12 which is implanted between the superior facet 22 of a first (lower) vertebra 20 and the corresponding inferior facet 32 of a second overlying vertebra 30. The shim portion has two opposed surfaces, a first (lower) surface 14 engaging the superior articular surface of the superior facet 22, and a second (upper) surface 16 engaging the inferior articular surface of the corresponding inferior facet 32. The opposed surfaces of the shim portion of the spinal facet cap can be substantially planar, as shown in FIG. 2, or they can be formed (e.g., concave or convex) to receive and at least partially complement or parallel superior and inferior facet contours.

From FIG. 2 it will be appreciated that the shim portion of the spinal facet cap must be properly aligned or positioned in the facet joint, and that this alignment must be maintained. An alignment portion is provided for this purpose. The alignment portion can be provided numerous ways in accordance with the invention. For example, the alignment portion can comprise an extension or tongue 18, having an orifice 19, to accept a screw or the like which is driven into the cortex of the vertebral pedicle. The alignment portion can also comprise one or more facet hooks and/or a ridge or boss disposed along the perimeter or margin of the shim portion, to engage the superior and/or inferior facets. The alignment portion at least partially encompasses the superior and/or inferior facet(s).

In some embodiments, the opposed surfaces are parallel (i.e., coplanar), such that the shim portion is of substantially uniform thickness. In other embodiments, the opposed surfaces are not coplanar, such that the shim portion is not of uniform thickness and is generally wedge-shaped. In embodiments where the opposed surfaces are not coplanar, the surfaces can be sloped along a common axis so as to form a simple angle. The angle separating the opposed surfaces can be, for example, from 0° (coplanar) to about 40°, preferably about 0° to about 20°. In other embodiments, the slopes of the opposed surfaces form a compound angle in which the slopes are not aligned on a common axis. It will be appreciated that the direction of slope is appropriately chosen to correct a facet joint for a given abnormality of curvature (e.g., kyphosis, lordosis, etc.).

It will be appreciated that a spinal facet cap according to the invention can be produced in a range of sizes and shapes by varying the thickness of the shim portion (i.e., distance between the opposed surfaces), the angle of the shim portion (i.e., angle between the opposed surfaces), the area of the shim portion (i.e., surface area of the opposed surfaces), and the shape of the shim portion and/or opposed surfaces so as to provide any desired amount of correction to a facet joint, and to accommodate any size of facet joint. Further, a facet cap according to the invention can be symmetrical or asymmetrical with respect to the angle, area, and shape of opposed surfaces.

Each opposed face of the shim portion is sized to accommodate the generally circular or oblong (i.e., oval) shape of the articulating surface of a facet joint into which the facet cap is inserted. The size or area of the opposed faces of a facet cap will depend on factors such as where in the spine the facet cap is implanted (e.g., cervical being smaller than lumbar), the age and size of the subject, and the condition of the facet joint. The size of the opposed faces is generally described herein as circular, having a diameter; however, it is to be understood that the opposed faces can be of any shape and the diameter refers to that portion of an opposed surface that substantially corresponds to an articular surface of a facet joint. The diameter of each opposed face of the shim portion ranges from about 5 mm to about 30 mm, preferably from about 10 mm to about 20 mm, still more preferably from about 12 mm to about 18 mm.

It will be appreciated that patients receiving facet caps can vary in age/size, and in degree of severity of scoliosis. Thus, the present invention contemplates a range of sizes and shapes of facet caps, to suit any facet joint in need of treatment, so as to correct any or all of a reduction in height, an abnormality in tilt, and an abnormality in angulation (e.g., kyphosis, lordosis) of the inferior or superior vertebral body. The facet caps can be provided ready for implanting (e.g., sterilized and appropriately packaged), or they can be sterilized prior to implanting using methods well-known in the art.

A spinal facet cap according to the invention can be made of any suitable biologically inert material. Examples of suitable materials are cobalt chrome, stainless steel, and titanium. Cobalt chrome is preferred owing to its biocompatibility with tissues and cartilage.

Several embodiments of the spinal facet cap of the present invention are shown in FIG. 3. For example, FIG. 3A shows a spinal facet cap like that shown in FIG. 2. In FIG. 3B, the shim portion 50 has an alignment portion comprising a ridge 54 disposed along the edge of and partially surrounding the surface 56 that engages the inferior facet, toward the tongue 52. As shown in FIGS. 3C and 3D, in which FIG. 3D shows a longitudinal section of the embodiment of FIG. 3C, the shim portion 60 similarly has an alignment portion comprising a ridge 68 on the edge of the surface 67 that engages the superior facet, opposite the tongue 62. The embodiment of FIGS. 3C and 3D also has a further ridge 64 on the edge of the surface 66 that engages the inferior facet, toward the tongue 62. It will be appreciated that the provision of an alignment portion comprising ridges on the first, second, or both surfaces of the facet cap helps to maintain alignment of the facet cap with the superior and inferior facets, and helps to keep the facet cap registered in the facet joint.

The alignment portion of a spinal facet cap according to the invention can also comprise one or more pins extending outwardly from at least one of the two opposed surfaces. For example, the spinal facet cap 70 shown in FIG. 3E has pins 72, 74 extending outwardly from the opposed surfaces 73, 75, respectively. The pins 72, 74 engage holes prepared in the articular surfaces of the superior and inferior facets during the implant procedure.

Figure 3A:
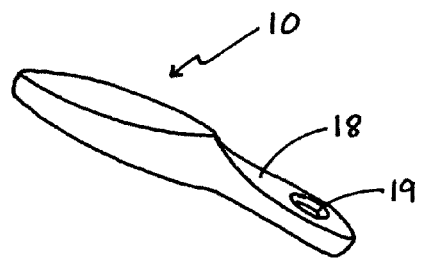
FIGS. 3A to 3F show further embodiments of a spinal facet cap according to the invention.
Figure 3B:
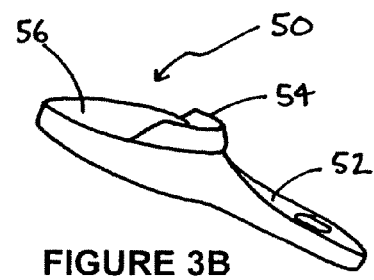
Figure 3C:
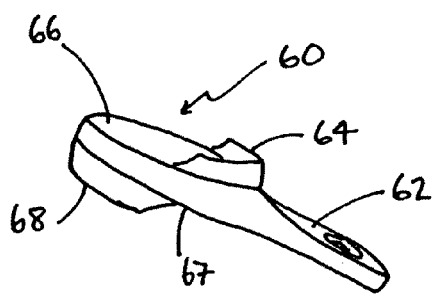
Figure 3D:
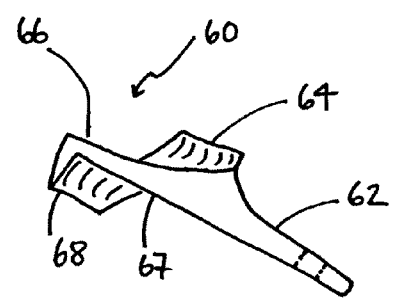
Figure 3E:
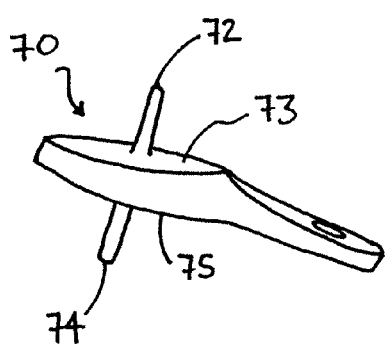
Figure 3F:
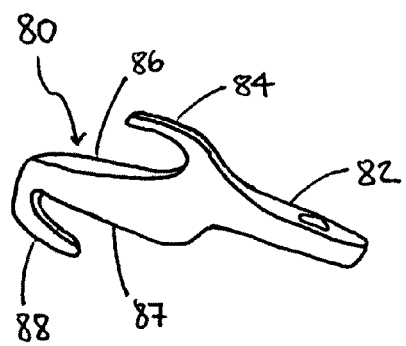

In FIG. 3F there is shown another embodiment of a spinal facet cap according to the invention in which the shim portion 80 has an alignment portion comprising a facet hook 88 on the edge of the surface 87 that engages the superior facet, substantially opposite the tongue 82, and another facet hook 84 on the edge of the surface 86 that engages the inferior facet, toward the tongue 82. In further embodiments, only one of either facet hook 84 or facet hook 88 is present. The facet hook can vary in the extent of the curvature of the hook and thus the extent to which the hook encompasses the inferior/superior facet. For example, in some embodiments the curvature of the facet hook can be reduced so that the hook extends from the shim portion in a 90° arc, whereas in other embodiments the hook extends from the shim portion in a 180° arc.

Although not shown in the drawings, it will be appreciated that embodiments of the invention such as those shown in FIGS. 3A to 3D and 3F can be provided with an orifice passing through the shim portion, for accepting a pin, screw, or the like driven through at least one of the inferior and superior facets, to thereby contribute to maintaining alignment of the spinal facet cap. In particular, in the embodiment of FIG. 3F, each of the facet hook 84, shim portion 80, and facet hook 88 can be provided with an orifice, the three orifices having a common longitudinal axis, so as to accommodate a pin or screw disposed through the facet hook 84, the inferior facet, the shim portion 80, the superior facet, and the facet hook 88. Also not shown in the figures are embodiments in which the shin, portion is sloped in the opposite direction to that shown (i.e., a directive relative to the tongue 18 in FIG. 3A).

Figure 4B:
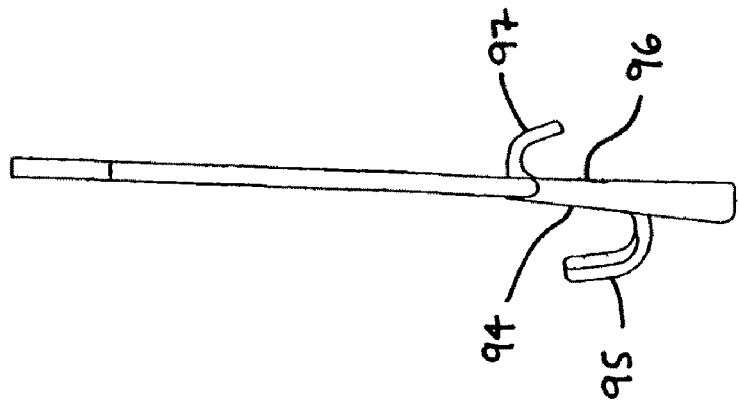
FIGS. 4A to 4C show a further embodiment of a spinal facet cap according to the invention.
Figure 4A:
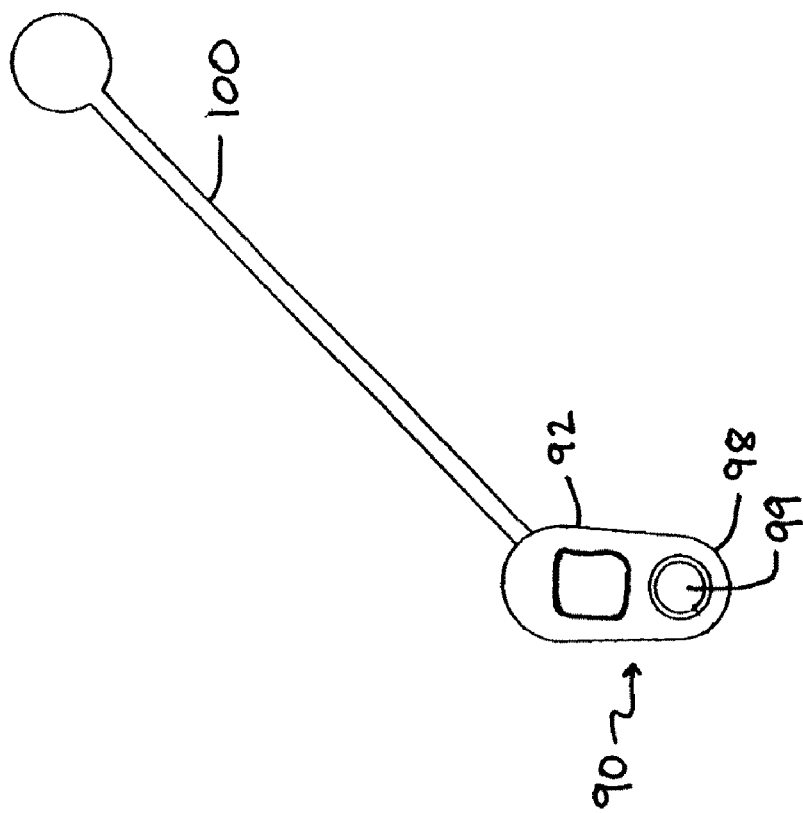
Figure 4C:
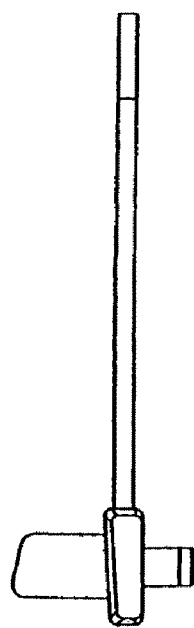
Figure 6B:
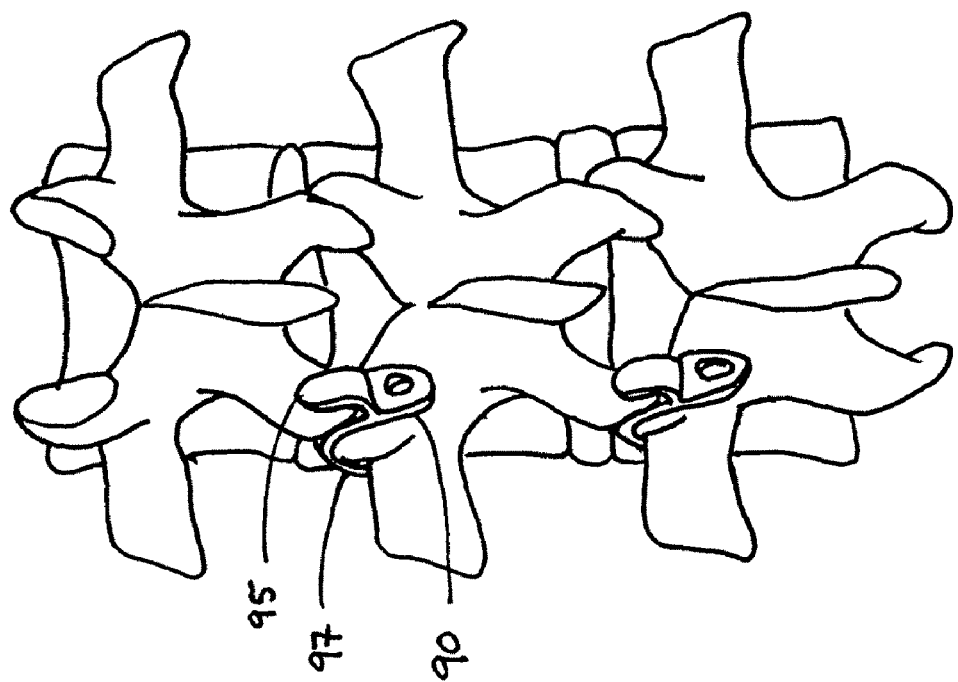
FIG. 6B shows a posterior view of the scoliotic spine of FIG. 5A corrected with spinal facet caps according to the invention.
Figure 6A:
FIG. 6A shows a posterior view of a scoliotic spine.

In the embodiment shown in FIGS. 4A to 4C, which is similar to that of FIG. 3F, the spinal facet cap 90 has a shim portion 92 with opposed surfaces 94, 96 provided with an alignment portion comprising facet hooks 95, 97, respectively, and a tongue 98. Tongue 98 extends outwardly from the shim portion 92, and has an orifice 99 for accepting a screw. Facet hook 95 engages the inferior facet, and facet hook 97 engages the superior facet. This can be seen in FIG. 6, which shows a scoliotic spine (FIG. 6A) in which the decrease in height and lateral tilt of the spine have been corrected with spinal facet caps according to the present embodiment (FIG. 6B). A handle 100 is optionally provided to facilitate implanting the facet cap. The handle 100 is attached to the facet cap in a manner to allow it to be removed upon implanting the cap. For example, the handle 100 can be crimped at the junction with the facet cap, so that it can simply be broken off once the facet cap is implanted.

It will be appreciated that the embodiment shown in FIG. 4 can be provided with only a single facet hook, in which case it is preferable that the facet hook 95 that engages the inferior facet is provided. However, the provision of two facet hooks 95 and 97 improves the stability of the implant. Also, the facet hooks can be wider or narrower than those shown in FIG. 4. A wider facet hook has the advantage of contacting more of the facet, and hence is preferable. When a very wide facet hook is provided, it can be curved so as to approximate the shape of the portion of the facet that it contacts, and hence contact a greater portion of the facet. As an alternative to a wide facet hook, a facet hook can comprise two or more fingers, the fingers providing multiple points of contact with a facet. An advantage of such fingers is that growth of tissue around and between the fingers is possible, and such growth improves the stability and reliability of the implant.

In a further embodiment, the distance between facet hooks, and/or the angle of the shim portion (i.e., the extent to which the shim portion is wedge-shaped) can be adjusted. An example of this embodiment is shown in FIG. 5. FIG. 5A shows this embodiment, denoted by reference numeral 120, in side and plan views, which comprises two parts 130 and 150. FIG. 5B shows part 130 in side and plan views, and FIG. 5C shows part 150 in side and plan views. Part 130 comprises a plate 134, an inferior facet hook 132 disposed on a first surface of the plate 134, and a tongue 140 and two rows of teeth 138 disposed on the opposite surface of the plate 134. An orifice 136 accommodates a cortical screw (not shown). Part 150 comprises a plate 154, a superior facet hook 152 disposed on a first surface of the plate 154, and two rows of teeth 158 disposed on the opposite surface of the plate 154. A longitudinal opening 156 is provided in the plate 154, for accepting the tongue 140 of part 130 in a sliding fit. As can be seen from FIG. 5A, part 130 mates with part 150 such that tongue 140 fits in opening 156 and teeth 138 mesh with teeth 158, and the inferior and superior facet hooks 132 and 152 are opposed. When mated, plates 134 and 154 comprise the shim portion. Preferably, the teeth comprising each set of teeth 138 and 158 are asymmetrical, such that meshing of the two sets of teeth forms a ratchet that allows parts 130 and 150 to slide relative to each other in one direction, but not the other. Preferably, such ratchet allows parts 130 and 150 to slide in a direction which brings the inferior and superior facet hooks closer together, and prevents the facet hooks from sliding further apart. Thus, to use this embodiment to correct a facet joint, parts 130 and 150 are first mated such that the facet hooks are farthest apart, and the so-assembled facet cap is inserted into a facet joint of a patient. The distance between the facet hooks is then reduced by sliding parts 130 and 150 together, to fit the facet joint being corrected and to provide the desired amount of correction. In variations of this embodiment, either or both of plates 134 and 154 can be wedge-shaped, so that as parts 130 and 150 slide relative to each other, the amount of shim provided to a facet joint can be adjusted. Further, such wedge-shape of part 130 and/or part 150 can be tapered in any direction relative to the facet hook, so as to provide correction for any type of facet joint asymmetry (e.g., lordosis, kyphosis, etc.). It will be appreciated that the facet hooks in this embodiment could be substituted for ridges, bosses, etc, as discussed in respect of the alignment portion of the above embodiments.

Figure 7B:
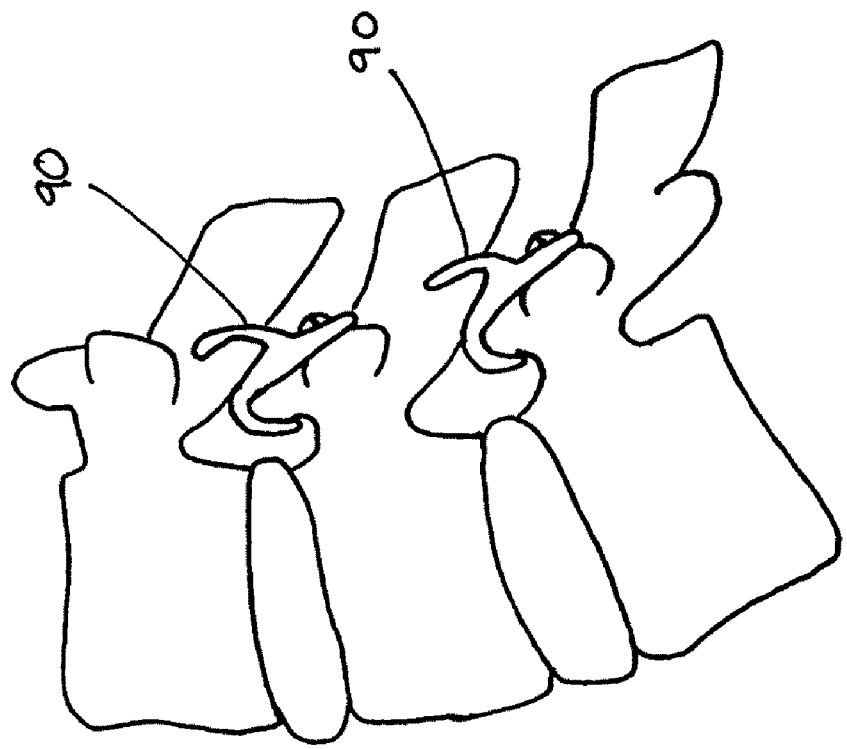
FIG. 7B shows a side view of the scoliotic spine of FIG. 7A corrected with spinal facet caps according to the invention.
Figure 7A:
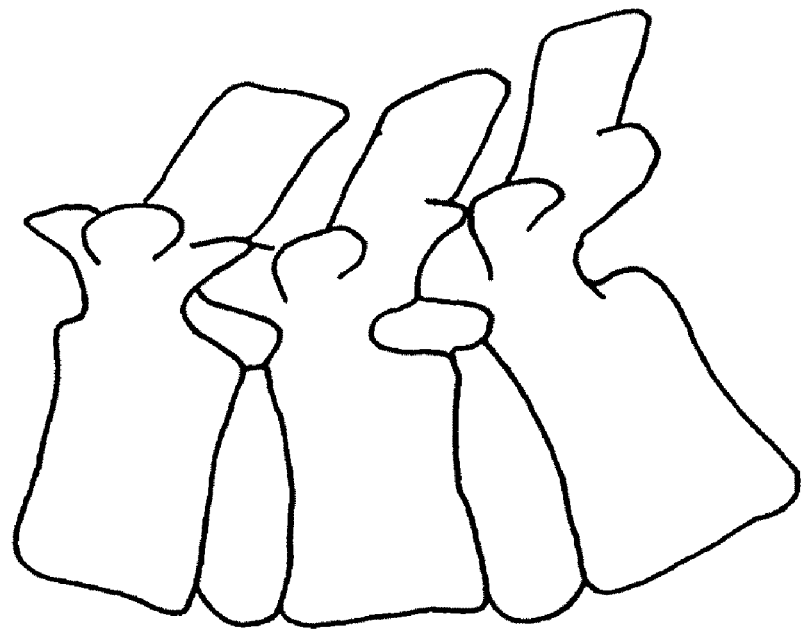
FIG. 7A shows a side view of a scoliotic spine.

FIG. 7A shows a side view of a scoliotic spine with pronounced lordosis. In FIG. 7B, the scoliosis shown in FIG. 7A has been corrected by inserting spinal facet caps 90 between facet joints. Here, spinal facet caps according to the embodiment shown in FIG. 3F or FIG. 4 are employed.

In another aspect, the invention provides a method for treating scoliosis by surgically implanting at least one spinal facet cap into at least one spinal facet joint, such that asymmetry between left and right facet joints of vertebrae is substantially or completely corrected.

Treating a subject exhibiting mild scoliosis might involve implanting only a single facet cap. Treating more severe scoliosis might involve implanting two or more spinal facet caps at various locations in the spine to achieve the desired correction. In such severe cases, spinal facet caps of various sizes and shapes are expected to be employed. As mentioned above, the invention provides for treating scoliosis while preserving facet joints. However, in some cases, some minor modification (e.g., providing a hole for a pin) or more extensive modification (e.g., removal of bone) of either or both of the inferior and superior facets might be necessary or desirable to ensure proper seating and alignment of a spinal facet cap, and hence improve the subject's prognosis. Treating a subject with scoliosis involves evaluating the subject prior to surgery and during surgery for the number, size, shape, location, and placement of spinal facet caps to achieve the desired correction. An imaging system (e.g., computed tomography (CT), radiography, or magnetic resonance imaging (MRI)) can advantageously be used to evaluate the subject prior to surgery, to help determine the number, size, shape, location, and placement of spinal facet caps to achieve the desired correction. Further, data obtained from such evaluation of a subject prior to surgery can be used to prepare a custom suite of facet caps of, for example, various sizes and shapes, to suit a particular subject.

WORKING EXAMPLES

Example 1

Cadaveric Implantation

A spinal facet cap based on the embodiment shown in FIGS. 2 and 3A, having a diameter of about 12 mm, was surgically implanted into the scoliotic spine of a cadaver (female, elderly) at the Department of Anatomy and Cell Biology at Queen's University, Kingston, Ontario, Canada, to evaluate the ease or difficulty of placement and the seating of the facet cap in the facet joint. There were no complications in implanting the facet cap into the spine, suggesting that use of the facet cap for treating scoliosis could become a routine surgical procedure. Moreover, during this exercise it was found that seating of the facet cap in the facet joint was fully satisfactory. This exercise therefore provides a strong indication that the spinal facet cap of the invention will be effective in the treatment of scoliosis.

Example 2

Prosthetic Model

Figure 8B:
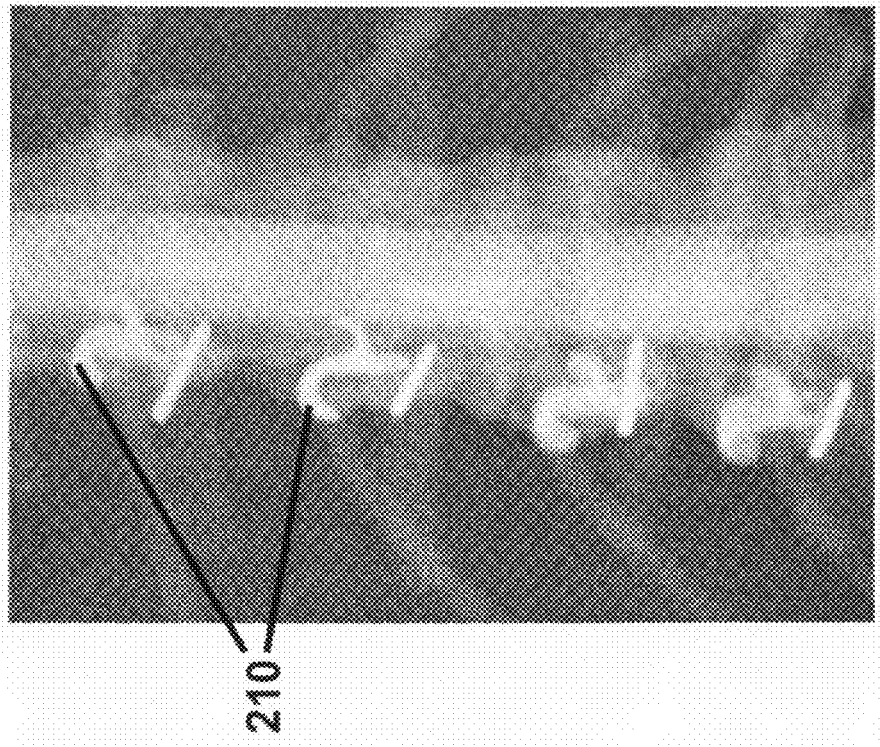
FIG. 8B is a radiograph of the model of FIG. 8A, with the scoliosis corrected using spinal facet caps of the invention.
Figure 8A:
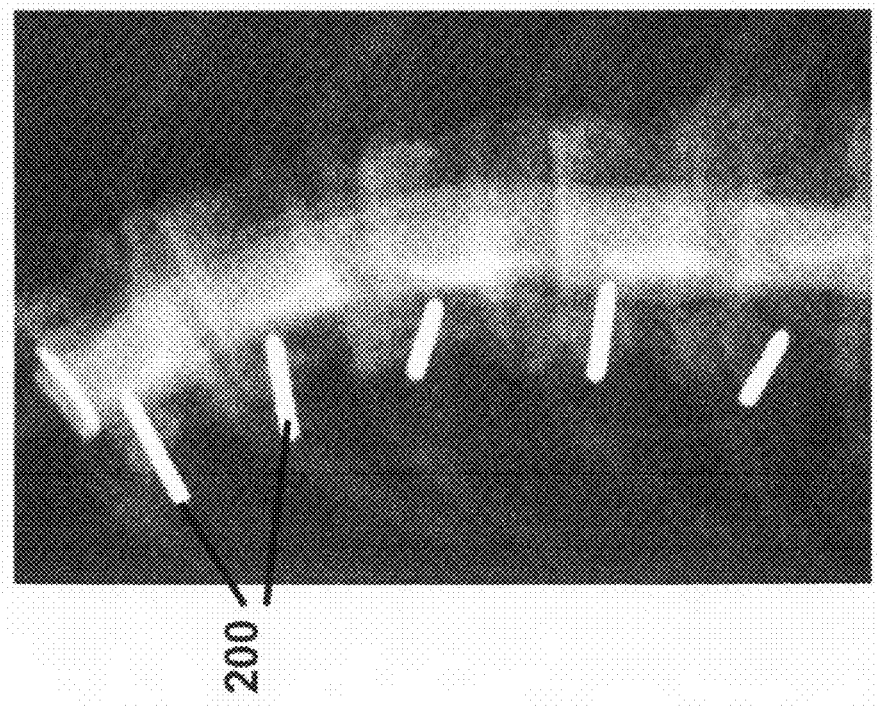
FIG. 8A is a radiograph of a prosthetic model of a spine with scoliosis at the mid-lumbar level.

Osteotomies were performed on the mid-lumbar facets of a prosthetic model of an adult human spine to create a scoliotic model. This is shown in the radiograph of FIG. 8A, where reference numeral 200 refers to pins used to hold the model together. Spinal facet caps like that shown in FIG. 3F were then inserted into the mid-lumbar facet joints, which substantially corrected the scoliotic curvature of the spine. This can be seen in the radiograph of FIG. 8B, where reference numeral 210 refers to the facet caps.

Example 3

Formulation of in vivo Placement

The success of cadaveric implantation led to the formulation of tempo in vivo application. During the course of standard scoliosis surgery, all facet joints from the superior to inferior aspect of the proposed fusion levels are stripped of the joint capsule, the cartilage removed, and the joint decorticated. Prior to destruction of the joints an in vivo model for facet cap placement is present, as no further dissection of the spine is necessary, in which the facet caps can be placed and removed in minutes. This has allowed the formulation of a working model for application of the facet caps. Thus, the below examples relate to the temporary insertion of facet caps during the course of standard corrective surgery, to establish an operative technique for their insertion, and to evaluate their efficacy and ease of use.

Example 4

Operative Technique

Pre-operative
Pre-operative planning is based on the standard standing radiograph of the spine. The most accessible inferior vertebral body demonstrating tilting relative to pelvis is identified. The inferior tilting of the vertebra is measured to determine the appropriate thickness of the shim portion and distance between facet hooks of the facet cap. The next superior adjacent facet may also be targeted as a sight for correction. More superiously in the spine the apex of the scoliotic curve is identified. A measurement of the interior tilt of this vertebra is obtained along the concave aspect of the scoliotic curvature. A facet cap having a shim of appropriate thickness and distance between facet hooks is placed at this level and the next superior adjacent facet may also be targeted.
Operative Technique
The patient is placed prone, supported by bolsters over ASIS and upper chest with care to keep pressure off the abdomen. After preparing the skin the back is draped to expose the midline of the back.
A midline incision is made over the spinous processes over the appropriate levels (see pre-operative planning). The linea between the left and right paravertebral muscles is dissected down to the spinous processes. Localization of the vertebral levels is checked by AP radiograph. The paravertebral muscles are then reflected laterally along the lamina to the facet joints. Care is taken to maintain the integrity of the facet ligaments. Further soft tissue dissection is then performed to expose the transverse processes.
The facet joint, which is to receive the facet cap, is then stripped of the joint capsule and posterior pericapsular ligament. Care is taken to leave the facet cartilage intact. The contra lateral facet joint is then stripped of ligament and capsule. The facet joint cartilage on the contra lateral facet joint is excised to bleeding subchondral bone. A laminar spreader is placed between the superior and inferior transverse processes on the side of the spine to receive the facet cap. The laminar spreader is distracted to open the space in the ipslateral facet joint. The facet cap is then placed in the facet joint and laminar spreader removed. Correct placement of the facet cap should allow for maintenance of the distraction created by the laminar spreader. The bone is then decorticated, autologus bone graft placed along both sides of the transverse processes, facet and lamina. AP and lateral radiographs are taken to assess position and affect of the facet cap. The paravertebral muscle is then approximated and skin closed.

Example 5

Male patient 16 years old with 70 degree thoracic curve and 95 degree neuromuscular kypho-scoliosis (Kingston, Ontario, Canada). The pre-operative plan for facet cap placement was to assess the possibility of seating a facet cap like that of FIG. 3F in the lumbar facet joint between the L1 and L2 lumbar vertebrae.
The posterior spine was prepared in the standard fashion, described above. After the L1-L2 lumbar vertebrae facet was stripped of the capsule the joint was inspected. No space was available to open the facet joint so that the facet cap could be inserted. However, it is expected that could the facet joint have been opened, the facet position could be altered to allow the facet cap to be seated.

Example 6

Female patient 14 years old with 54 degree King II idiopathic scoliosis (Kingston, Ontario, Canada). The pre-operative plan was for facet cap placement in the L1-L2 lumbar facet joint, and the T6-T7 thoracic facet joint. The use of laminar spreader distraction between the facet joint aided in facet joint alignment, as did the addition of a small metal dissector into the joint for space creation and facet cap placement.
The posterior spine was prepared in the standard fashion as described above. After the L1-L2 lumbar vertebrae facet was stripped of the capsule, a blunt osteotome was placed in the inferior joint and wedged the joint open. Concurrently a laminar spreader was placed between L1 and L2 and distracted. These two manoeuvres opened the facet joint and subjectively corrected the scoliosis in this segment. However, the facet cap like that of FIG. 3B could not be inserted because it was the wrong size for this patient. In particular, the facet hook pattern (radius) of the superior and inferior facet hooks of the facet cap was too narrow and the overall length of the facet cap too long. It is expected that changing the radius of the facet hooks to a range of about 5 mm to about 1 cm, and the overall length of the facet cap to a range of about 1.5 cm to about 2.5 cm would have been appropriate. The thoracic facet was addressed, and it was found that the superior facet hook obscured implantation of the facet cap in this patient and the facet cap could not be inserted. It is expected that rotation of the inferior facet hook by about 30 degrees from parallel to the facet cap to the right, for right insertion, and to the left for left insertion, would have facilitated implantation of the facet cap in this patient.

Example 7

Female patient 16 years old with 45 degree thoracic curve and 95 degree kyphosis neuromuscular kypho-scoliosis (Kingston, Ontario, Canada). The pre-operative plan was to place modified facet caps (FIGS. 9A and 9B) into the L2-L3 lumbar facet joint and T7-T8 thoracic facet joint.

The posterior spine was prepared in the standard fashion, described above. Using the technique described above the L2-L3 facet joint was opened and a facet cap like that shown in FIG. 9B was inserted. This is shown in FIG. 10B, where reference numeral 400 refers to the facet cap, with superior facet hook 410 and inferior facet hook 420 partially visible. Also shown in FIG. 10B are several Moss® Miami (DePuy-AcroMed Inc.) laminar hooks 430 placed around vertebral laminae, for use with rods for the standard corrective procedure. The facet cap subjectively corrected the scoliosis at this level. The T7-T8 facet joint was prepared and a facet cap like that shown in FIG. 9A was inserted, as shown in FIG. 10A where reference numeral 300 denotes the facet cap. The inferior facet hook 320 can be seen clearly. Also visible are several Moss® Miami (DePuy-AcroMed Inc.) laminar hooks 330 placed around vertebral laminae, for use with rods for the standard corrective procedure. The facet cap subjectively corrected the scoliosis at this level. Dimensions of the facet caps used in this example are provided in the below table.

TABLE 1

Figure 9A:
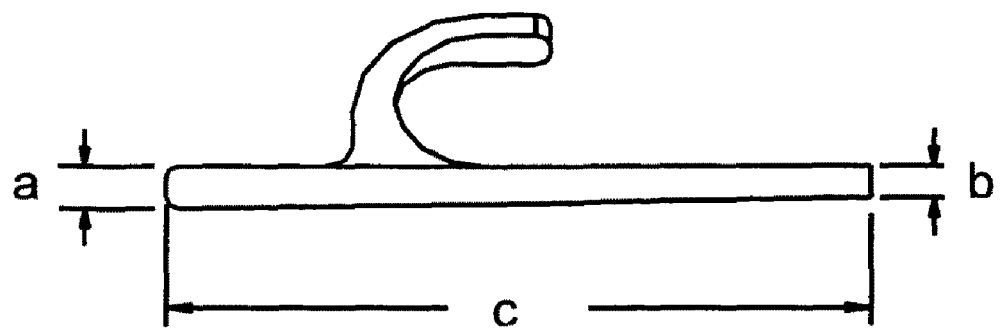
FIGS. 9A and 9B show embodiments of a facet caps according to the invention.
Figure 9B:
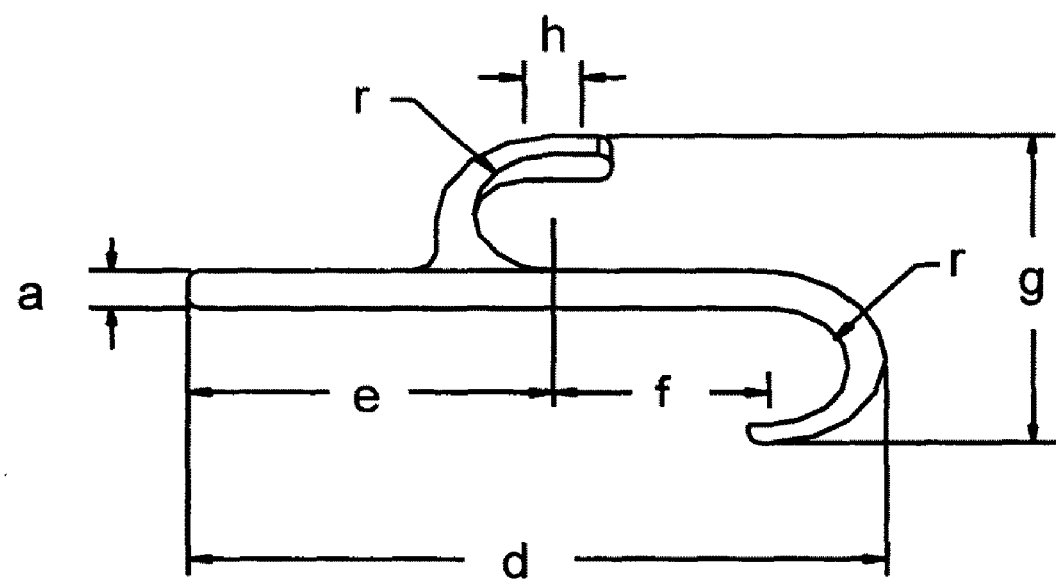
Figure 10B:
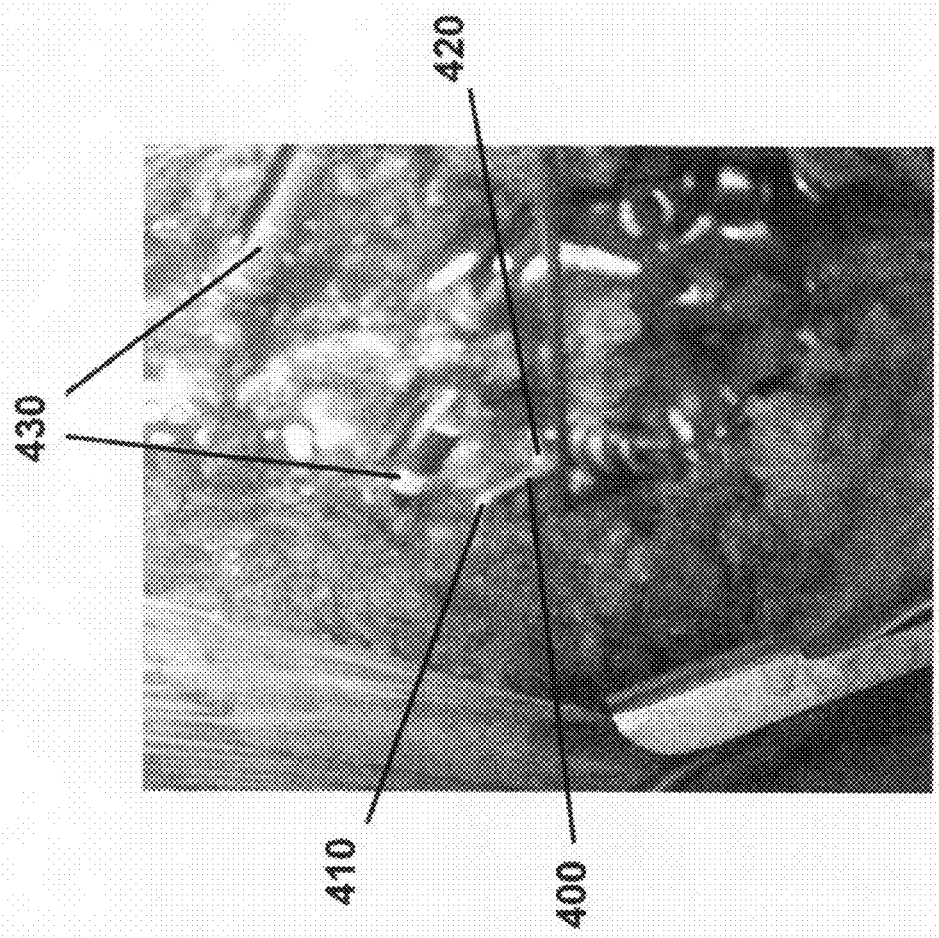
FIGS. 10A and 10B are photographs showing the facet caps of FIGS. 9A and 9B, respectively, inserted into facet joints of a patient.
Figure 10A:
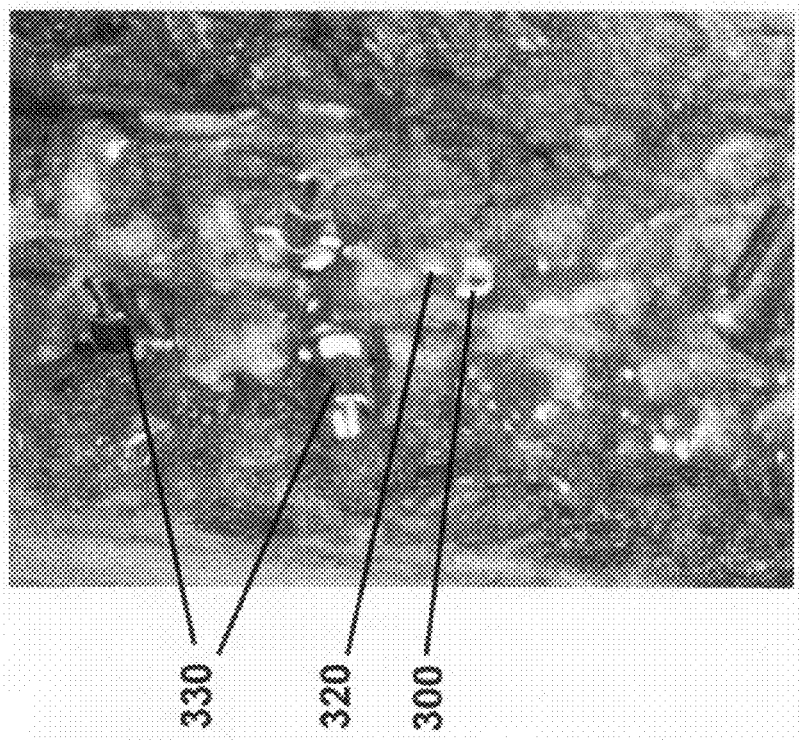

Dimensions of facet caps used in Example 7 and shown in FIGS. 9A and 9B. Width of both facet caps was about 12.7 mm.

| Dimension | mm |
|---|---|
| a | 2.0 |
| b | 1.5 |
| c | 25.0 |
| d | 28.0 |
| e | 14.7 |
| f | 8.7 |
| g | 8.4 |
| h | 0 |
| r | 3.2 |

EQUIVALENTS

Variants to the embodiments described above will be apparent to those skilled in the art. Such variants are within the scope of the present invention and are covered by the below claims.

We claim:

1. A prosthetic device, comprising:
a shim adapted to be inserted into a facet joint of the spine, the shim including substantially opposed surfaces adapted to engage articular surfaces of the facet joint;
means extending from the shim that maintains alignment of the shim within the facet joint by receiving and partially encircling part of either a superior facet or an inferior facet; and
a portion extending from the shim, the portion having an opening and adapted to be fixed to a vertebral structure associated with at least one of the superior facet or the inferior facet of the facet joint;
wherein the portion is adapted to be fixed to the vertebral structure with a screw or a pin.

2. The prosthetic device of claim 1, wherein thickness of the shim can be varied or the opposed surfaces are at least partially complementary to articular surfaces of the facet joint.

3. The prosthetic device of claim 1, wherein the means that maintains alignment of the shim comprises at least one facet hook extending from the shim, the at least one facet hook adapted to receive and partially encircle part of either the superior facet or the inferior facet of a vertebra.

4. The prosthetic device of claim 3, wherein the at least one facet hook includes a curve that receives and partially encircles part of either the superior facet or the inferior facet of the facet joint.

5. The prosthetic device of claim 4, wherein the at least one facet hook is curved in a direction that at least partially overlies a said opposed surface of the shim.

6. The prosthetic device of claim 3, comprising at least two facet hooks, the at least two facet hooks having curves that receive and partially encircle part of either the superior facet of the facet joint or the inferior facet of the facet joint.

7. The prosthetic device of claim 3, comprising at least two facet hooks, a first facet hook having a curve that receives and partially encircles part of the superior facet of the facet joint, and a second facet hook having a curve that receives and partially encircles part of the inferior facet of the facet joint.

8. The prosthetic device of claim 1, wherein the means for maintaining alignment of the shim comprises:
at least one facet hook extending from the shim, the at least one facet hook adapted to receive at least a portion of either the superior facet or the inferior facet of a vertebra.

9. The prosthetic device of claim 8, wherein the at least one facet hook includes a curve that receives at least a portion of either the superior facet or the inferior facet of a vertebra.

10. The prosthetic device of claim 1, wherein said means includes structure that maintains alignment of the shim within the facet joint, said structure being rotated or twisted relative to the shim.

* * * * *

UNITED STATES PATENT AND TRADEMARK OFFICE
CERTIFICATE OF CORRECTION

| | | |
|---|---|---|
| PATENT NO. | : 8,070,777 B2 | Page 1 of 1 |
| APPLICATION NO. | : 12/068850 | |
| DATED | : December 6, 2011 | |
| INVENTOR(S) | : Donald A. Soboleski, Gerald A. B. Saunders and Daniel P. Borschneck | |

It is certified that error appears in the above-identified patent and that said Letters Patent is hereby corrected as shown below:

Column 12, Claim 6, Line 28, delete the word "partially".

Signed and Sealed this
Twentieth Day of March, 2012

David J. Kappos
*Director of the United States Patent and Trademark Office*